(12) United States Patent
Gutsol et al.

(10) Patent No.: US 8,334,422 B2
(45) Date of Patent: Dec. 18, 2012

(54) METHOD AND DEVICE FOR AIR DISINFECTION AND STERILIZATION

(75) Inventors: Alexander F. Gutsol, San Ramon, CA (US); Alexander Fridman, Marlton, NJ (US); Michael J. Gallagher, Philadelphia, PA (US); Victor Vasilets, Moscow (RU); Kenneth Blank, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 137 days.

(21) Appl. No.: 12/377,904

(22) PCT Filed: Aug. 15, 2007

(86) PCT No.: PCT/US2007/075973
§ 371 (c)(1),
(2), (4) Date: Jul. 14, 2009

(87) PCT Pub. No.: WO2008/097347
PCT Pub. Date: Aug. 14, 2008

(65) Prior Publication Data
US 2010/0168499 A1    Jul. 1, 2010

Related U.S. Application Data

(60) Provisional application No. 60/822,885, filed on Aug. 18, 2006, provisional application No. 60/871,045, filed on Dec. 20, 2006.

(51) Int. Cl.
*A62D 3/19* (2007.01)
*A61L 9/16* (2006.01)
(52) U.S. Cl. ............................. 588/311; 422/22; 422/186
(58) Field of Classification Search .................. 588/301, 588/311; 422/22, 186; 204/164
See application file for complete search history.

(56) References Cited

U.S. PATENT DOCUMENTS

| 6,030,506 A | 2/2000 | Bittenson et al. |
| 6,159,422 A | 12/2000 | Graves et al. |
| 7,037,468 B2 * | 5/2006 | Hammerstrom et al. ....... 422/22 |
| 7,192,553 B2 | 3/2007 | Crowe et al. |
| 2003/0106788 A1 | 6/2003 | Babko-Malyi |

(Continued)

FOREIGN PATENT DOCUMENTS
CN    02655913 Y    11/2004
(Continued)

OTHER PUBLICATIONS

Broadwater et al., "Sensitivity of three selected bacterial species to ozone", Applied Microbiology, 26(3), Sep. 1973, 391-393.

(Continued)

*Primary Examiner* — Wayne Langel
*Assistant Examiner* — Syed Iqbal
(74) *Attorney, Agent, or Firm* — Woodcock Washburn, LLP (57) ABSTRACT

A method for decontaminating bioaerosol with high concentrations of bacterial, viral, spore and other airborne microorganisms or biologic contaminants, in flight at high flow rates. A plasma screen created across the flow of air contaminated with airborne biologic agents renders contaminants non-culturable within millisecond. The technology may cooperate with heating, ventilation, and air conditioning (HVAC) systems. It may be particularly beneficial in preventing bioterrorism and the spread of toxic or infectious agents, containing airborne pandemic threats such as avian flu, sterilizing spaces such as hospitals, pharmaceutical plants and manufacturing facilities, treating exhaust ventilation streams, minimizing biological environmental pollutants in industrial settings, improving general air quality, and preventing sick building syndrome.

10 Claims, 5 Drawing Sheets

U.S. PATENT DOCUMENTS

| | | |
|---|---|---|
| 2003/0175180 A1 | 9/2003 | Shannon |
| 2004/0005261 A1 | 1/2004 | Ko |
| 2004/0022669 A1 * | 2/2004 | Ruan et al. ............ 422/22 |
| 2004/0037736 A1 | 2/2004 | Perruchot et al. |
| 2004/0050684 A1 | 3/2004 | Babko-Malyi et al. |
| 2005/0023128 A1 | 2/2005 | Keras et al. |
| 2006/0280646 A1 | 12/2006 | Siosawa |

FOREIGN PATENT DOCUMENTS

| | | |
|---|---|---|
| WO | WO03063914 A3 * | 7/2003 |
| WO | WO 03/063914 A3 | 8/2003 |
| WO | WO 2005/087984 A1 | 7/2005 |
| WO | WO 2006/003382 A1 | 1/2006 |

OTHER PUBLICATIONS

Burleson et al., "Inactivation of viruses and bacteria by ozone, with and without sonication", Applied Microbiology, 29(3), Mar. 1975, 340-344.

Cown et al.. "The critical-orifice liquid Impinger as a sampler for bacterial aerosols", Applied Microbiology, Oct. 5, 2008, 1956, 119-124.

Ehresmann et al., "Effect of relative humidity on the survival of airborne unicellular algae", Applied Microbiology, 29(3), Mar. 1975, 352-357.

Enserink "The Trypanosomatid Genomes", Science: Current Awareness Issue, 309(5733). Jul. 15, 2005, downloaded Oct. 7, 2009, www.sciencemag.org, 3 pages.

Fridman et al., "Blood coagulation and living tissue sterilization by floating-electrode dielectric barrier discharge in air", Plasma Chemistry Plasma Processing, 26, Jun. 15, 2006, 425-442.

Gallagher at al., "Non-thermal plasma applications in air-sterilization", International Symposium on Plasma Science, Aug. 2005, 5 pages.

Gangoli at al., "Rotating Non-Equilibrium gliding arc plasma disc for enhancement in Ignition and combustion of hydrocarbon fuels", ISPC-17, Aug. 7-12, 2005, Toronto, Canada, 6 pages.

Garamoon et al., "Experimental Study of Ozone Synthesis", Plasma Sources Science and Technology, May 17, 2002, 11, 254-259.

Harstad "Evaluation of air filters with submicron viral aerosols and bacterial aerosols", American Industrial Hygiene Association Journal, May-Jun., 1969, 280-290.

Hatch et al., "Physiological responses of airborne bacteria to shifts in relative humidity", Bacteriological Reviews, 30(3), Sep. 1966, 597-602.

Heidelberg et al., "Effect of aerosolization on culturability and viability of gram-negative bacteria", Applied and Environmental Microbiology, 63(9), Sep. 1997, 3585-3588.

Ishizaki et al., "Inactivation of bacillus spores by gaseous ozone", Journal of Applied Bacteriology, 60, 1986. 67-72.

Jaieinghani "Bactericidal properties of electrically enhanced HEPA filtration and a bioburden case study". InterPhex Conference, New York, NY, Apr. 20-22, 1999. 261-270.

Kelly-Wintenberg et al., "Air filter sterilization using a one atmosphere uniform glow discharge plasma (the Volfilter)", IEEE Transactions on Plasma Science, 28(1), Feb. 2000, 64-71.

Khadre et al., "Microbiological aspects of ozone applications in food: a review", Journal of Food Science, 66(9) 2001, 1242-1252.

Kowalski et al., "Demonstration of a hermitic airborne ozone disinfection system: studies on $E.\ coli$", American Industrial Hygiene Association Journal, Mar.-Apr. 2003, 64, 222-227.

Laroussi, "Program of the Thirty-Seventh Annual Meeting of the Division of Plasma Physics", Bull. Amer. Phys. Soc. Div. Plasma Phys, Nov. 6-10, 1995, Louisville, Kentucky, 40(11), Oct. 1995, 1685-1686.

Laroussi, "Sterilization of Contaminated Matter with an Atmospheric Pressure Plasma", IEEE Transactions on Plasma Science, 24(3), Jun. 1996, 1188-1191.

Moisan et al., "Low-temperature sterilization using as plasmas: a review of the experiments and an analysis of the inactivation mechanisms", International Journal of Pharmaceutics, May 25, 2001, 226, 1-21.

Moreau et al., "Lethal effect of the gliding arc discharges on *Erwinia spp*.", Journal of Applied Microbiology, 98, 2005, 1039-1046.

United States General Accounting Office report to the Honorable Bill Frist, Majority Leader, U.S., Senate, "Public health response to anthrax incidents of 2001", Bioterrorism. Oct. 15, 2003, 48 pages.

Von Guten, "Ozonation of drinking water: part II. Disinfection and by-product formation in presence of bromide, iodide or chlorine", Water Research, 2003, 37,1469-1487.

* cited by examiner

METHOD AND DEVICE FOR AIR DISINFECTION AND STERILIZATION

CROSS-REFERENCE TO RELATED APPLICATIONS

This application is the National Stage of International Application No. PCT/US2007/075973 filed Aug. 15, 2007, which claims the benefit of U.S. Provisional Application No. 60/822,885, filed Aug. 18, 2006, and U.S. Provisional Application No. 60/871,045, filed Dec. 20, 2006, the entire disclosure of each application is incorporated by reference herein.

STATEMENT OF GOVERNMENT INTEREST

This invention was reduced to practice with Government support a U.S. Army Medical Research Acquisition Activity; Cooperative Agreement W81XWH 04-1-0419. The Government is therefore entitled to certain rights to this invention.

BACKGROUND OF THE INVENTION

1. Field of the Invention

This invention is directed to a method and device for decontaminating high concentrations of bacterial bioaerosols, viral bioaerosols and other airborne microorganisms in flight at high flow rates. The invention is particularly applicable to the Heating, Ventilation and Air Conditioning (HVAC) industry and bioterrorism defense industry.

2. Description of the Related Technology

The escalating threat of airborne biologic and bioterrorism agents, present a need for robust technologies and methods to mitigate the spread of airborne contaminants. Events such as the avian flu pandemic, the 1976 Legionnaires outbreak in Philadelphia and the 2001 anthrax terrorism in the United States demonstrate the ability to rapidly spread biologic contaminants through ventilation systems.

To address these concerns, scientists are focusing on non-thermal plasma-based technologies, which have previously proven successful in deactivating microorganisms, such as viruses and bacteria, in solution and on surfaces. Plasma has proven to be useful as a microbial disinfectant in many surface sterilization studies and it can be delivered with low power consumption, as a non-thermal discharge that is relatively easy to construct requiring simple power supplies.

Decontamination of microorganisms in flight using non-thermal plasma technology, however, has not been effectively implemented. Plasma-based air decontamination has only been found effective when coupled with high efficiency particulate air (HEPA) filters, which trap and kill microorganisms. HEPA filters, however, are inefficient at trapping submicron-sized airborne microorganisms. Moreover, HEPA filters also cause significant pressure losses in heating, ventilation, and air conditioning (HVAC) systems, generating high energy and maintenance costs. The filters function as a surface on which contaminants are captured; therefore, the prior art methodologies are, in essence, the same as standard plasma surface sterilization. Numerous technologies, such as those disclosed in Chinese Patent no. 02655913Y, U.S. Patent application publication no. 2004/0037736A1 and International patent application publication nos. WO 03/063914 A2, WO 05/067984 and WO 06/003382 A1, similarly sterilize air by directing plasma emissions at a filter surface, which entraps the biologic contaminants.

Apart from treatments in solution or on surface, there remains a need to develop a means for in flight plasma-based decontamination so as to be able to deactivate microorganisms in the air while in motion. This may be particularly useful for sterilizing ventilation systems and preventing the spread of airborne biologic agents.

In Michael J. Gallagher, et. al., "Non-Thermal Plasma Applications in Air-Sterilization," *International Symposium on Plasma Science* (August 2005), a non-thermal plasma emission device and method for treating airborne biologic contaminants was proposed, but neither tested nor sufficiently described such that one of ordinary skill in the art would be able to reproduce the proposed technology and in flight plasma sterilization methodology. The publication discloses a calibration test using a Pathogen Detection and Remediation Facility (PDRF) incorporating a plasma emission device such as a Dielectric Barrier Discharge (DBD) device or a Magnetically-Rotated Gliding Arc (MRGA) device. The calibration experiment involved emission of cyanobacterial aerosol to identify bioaerosol losses from diffusion, inertia and evaporation to establish accurate controls before applying non-thermal plasma. Additionally, the publication proposes, but does not describe, sterilization experiments with cyanobacteria and influenza A virus. The publication does not apply plasma to the cyanobacteria calibration experiments.

Based on the known efficiency of plasma-based sterilization technology, it is unexpected that it would be possible to render a substantial proportion of biologic agents inactive in flight in a short time, such as milliseconds, using non-thermal plasma. By comparison, DBD surface sterilization treatment times are often 1000 times longer, on the order of seconds, and in some cases even minutes in duration.

Therefore it would be desirable to develop a method capable of efficiently sterilizing airborne biologic agents within a period of milliseconds.

SUMMARY OF THE INVENTION

The invention is directed to a method for sterilizing biologic agents in a gaseous media. In one aspect, the invention is a method for treating culturable *E. coli* in a moving air stream at high airflow rates with plasma so as to achieve a substantial reduction in active bacteria within a period of milliseconds.

In another aspect, the invention is directed to a method for effectively sterilizing concentrated bacterial bioaerosols in a moving air stream at high airflow rates with plasma.

In another aspect, the invention cooperates with a Heating, Ventilation and Air Conditioning (HVAC) system for one or more of the purposes of preventing bioterrorism, preventing the spread of contagious or toxic agents, containing airborne pandemics, sterilizing spaces and buildings, treating exhaust ventilation streams, minimizing environmental pollutants, improving general air quality and preventing sick building syndrome.

DETAILED DESCRIPTION OF THE PREFERRED EMBODIMENTS

Non-thermal plasma is an electrically neutral mixture of atoms, molecules, electrons and ions that cannot be described by one temperature. Average energy of electrons in non-thermal plasma is usually on the level of more than 1 electron-volt (eV), (1 eV corresponds to temperature of about 11,600 K), while average translational temperature of heavy particles (ions, molecules and atoms) is much less, usually below 3,000 K and often is very close to ambient (room) temperature, e.g. 20° C.

For the purpose of this invention it is possible to consider a biological agent as an active one if it is capable of reproduction or proliferation (so-called culturable microorganisms) in a special appropriate media or in human organism. If microorganism is not able to reproduce itself (is not culturable), it is highly probable that it cannot harm another organism even if its structure is mechanically intact, and thus such microorganisms are considered to be inactivated.

This invention is directed to a method for sterilizing biologic contaminants entrained, dispersed or suspended in a gaseous media at high flow rates by plasma emissions and a system for carrying out the method.

One system of the invention may include a Pathogen Detection and Remediation Facility (PDRF) and a plasma emission device, which renders biologic contaminants non-culturable. The PDRF, as shown in FIG. 1, is a specialized plug flow reactor that is capable of circulating and sampling a gaseous media as well as bioaerosol generation, capture and containment. It is designed to operate at high airflow rates of about 25 L/s or greater, which are typical for indoor ventilation systems. A centrifugal blower 2 drives and circulates the contaminated gaseous media through a mixing chamber 3 and ventilation line 1. In a preferred embodiment, the PDRF is a closed system that allows for humidity control, which may be set to optimize sterilization capabilities. The air pressure and temperature within the line is regulated by a pressure release value 4 and hygrometer/thermometer 5. One of the primary advantages of the PDRF recirculating airflow system the ability to repeatedly treat bioaerosols, entrained, dispersed or suspended in a gaseous media, recirculating through the plasma emission device 6. The system also includes a bioaerosol nebulizer 7 and compressed air source 8 for the purposes of introducing a sample of biologic contaminants entrained, dispersed or suspended in a gaseous media.

The plasma emission device 6 may include any mechanism capable of producing plasma in a directed air or aerosol stream. In a preferred embodiment, the device may be a Dielectric Barrier Discharge ventilation grating (DBDG) plasma device or a Magnetically-Rotated Gliding Arc (MRGA) device. FIG. 2 shows a DBDG device 6, which includes a pair of comb-like electrodes inserted one into another 16 DBDG consists of two comb-like gratings (grills) inserted one into another. 1-mm wires 13 of one grating are covered with quartz capillaries of 2 mm outer diameter and connected to a high voltage AC power supply 15. There are 1.5 mm air gaps between these insulated wires and 1-mm bare wires 13 of the second grating that are grounded. When high-voltage AC power supply is on, non-equilibrium plasma is generated in the air gaps between bare and insulated wires, connected to a high voltage source 15, air sampling ports 9, connected to a set of liquid impingers 12 and a vacuum source 14.

In a preferred embodiment, a DBD device 6 is use to generate plasma. The DBD is an alternating current discharge between two electrodes 16, at least one of which is covered by a dielectric. DBD plasma can be formed in the gas filled area, otherwise known as the discharge gap, between one electrode and a dielectric or between two dielectrics. The DBD is driven by an applied alternating high voltage (several kilovolts), which generates a high electric field between the electrodes 16. In the absence of a dielectric, the discharge starting from the first spark, would rapidly progress to an arc, as the electrons in the spark would initiate a series of ionization events, leading to very high current and ultimately to arc formation. The dielectric prevents arc formation by accumulating charge on the surface and generating an electric field that opposes the applied field, thereby limiting the current and preventing development of an uncontrolled discharge. Alternating high voltage polarities ensures formation of this discharge in each half of the voltage cycle.

Usual DBD devices 6 operate in the kilohertz range, so plasma between the electrodes 16 does not have enough time to extinguish completely. In one embodiment, the non-thermal plasma discharge is generated by a high frequency oscillation of high voltage that is from about 1 to about 20,000 kHz, optionally, from about 5 to about 30 kHz, and a peak-to peak voltage of about 1 to about 50 kV, optionally, from about 5 to about 30 kV.

As a gaseous media in which biologic contaminants are entrained, dispersed or suspended is introduced into the DBD device 6 through an entry port 10, a quasi-sinusoidal waveform, as shown in FIG. 3, is generated by a quasi-pulsed high-voltage source and applied across the electrode gaps generating a high electric field and non-equilibrium plasma that covers the whole area between electrodes 16. The period between pulses is approximately 600 μs, peak-to-peak voltage is 28 kV, and current reaches nearly 50 amps in a pulse. The average power of the discharge is approximately 330 watts and considering the discharge area of 91 $cm^2$, the power density is 3.6 watts/$cm^2$. The majority of power is discharged in the very short duration of the pulse itself, which has a period of 77 μs and average pulse power of 2618 W. Since the residence time of a bioaerosol particle passing through the discharge area is 0.73 ms and the period between pulses is 0.6 ms, this means that each bioaerosol particle that passes through the DBD discharge experiences about 1 pulse of DBD discharge power, assuming the discharge is fairly uniform and gaps between streamers are not considered. The air passes through the plasma stream and leaves the DBD through an exit port 11. In a preferred embodiment, the plasma "curtain" that is created should not have large holes, e.g. larger than distance between DBD surfaces. The time between high voltage pulses that generate plasma should not be significantly larger then the residence time of air in plasma $t=Sd/Q$, where S is the free area where plasma is generated, d is the thickness of the bare electrodes and Q is the air flow rate. The power should be sufficient to provide the desired degree of sterilization.

The higher the power, the greater the degree of sterilization. For example, an instantaneous decrease in *E. Coli* concentration of a factor of 30 is observed at an energy input of about 330 W/25 l/s=13.2 J/l (joule per liter). Thus, about 27 J/l should provide a 3 log reduction in *E. Coli* concentration, 9 J/l should provide a 1 log reduction and 54 J/l should provide a 6 log reduction in plasma. Additional sterilization may also occur in the post-plasma treatment flow. Accordingly, preferred ranges for operation are about 3-100 J/l and, more preferably, 5-30 J/l.

Figure 4:
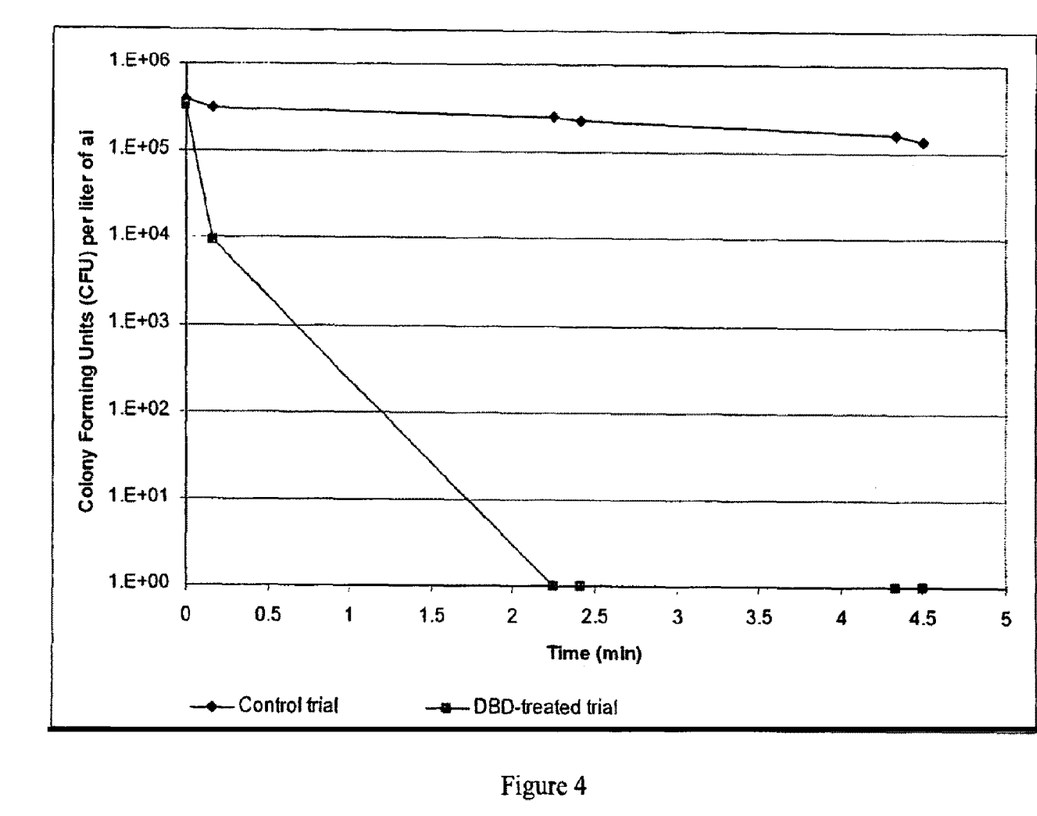
FIG. 4 is a graph of colony forming units versus time showing the results of DBD-treated *E. Coli* in a PDRF system in three replicate trials.

The method of the present invention involves sterilizing biologic contaminants entrained, dispersed or suspended in a gaseous media by circulating contaminated gaseous media through a stream of plasma. Microorganisms are rendered inactive within milliseconds and the contaminants do not have to adhere or contact a surface to enable sterilization. Flow rates can be increased by increasing input power. The residence time should be sufficient to ensure that at least one current pulse occurs during the residence time to thereby ensure plasma treatment of all flow. More preferably, the time between plasma generation pulses should be less than the residence time, and more preferably, less than half the residence time. In comparison to currently known methods for air sterilization, the present invention enables sterilization of biologic agents in a gaseous flowing media without the use of filters or other sterilization surfaces. This is unexpected since plasma sterilization in a gaseous flowing media is significantly more difficult and challenging than sterilization in solution or on a surface because of the very short residence time of microorganisms in the plasma zone. The methods of the prior art are therefore unable to explain the single run, 2-log reduction in viable *E. Coli* population. Additionally, based on the prior art and theoretical models, one of ordinary skill in the art would expect efficiency returns of in flight plasma based sterilization to be no more than about 15% after one application of plasma emission for the experiment described above. The 97% efficiency of bacteria inactivation shown in FIG. 4, is therefore quite surprising. Moreover, the invention only requires a minimal amount of energy for operation, resulting in low operational costs.

Experimental experience shows that is very difficult to create bio-contamination in large volume of air with concentration higher than 1,000,000 particles per 1 liter. Thus, a 5 or greater log reduction should be sufficient to prevent consequences of a biological attack. In other cases (pandemic, sick building syndrome) disinfection may typically be accomplished by a 3 or greater log reduction.

It is envisioned that this technology will be used to improve air ventilation and sterilization by deactivating airborne microorganisms. The technology is particularly well suited for applications in heating, ventilation and air conditioning (HVAC) systems. More specifically, the invention may be used in the bioterrorism defense industry to prevent the spread of toxic or infectious agents, contain airborne pandemics such as avian flu, sterilize various spaces such as hospitals, pharmaceutical plants and manufacturing facilities, treat exhaust ventilation streams, minimize environmental pollutants in industrial settings, improve general air quality, and prevent sick building syndrome.

EXAMPLES

Example 1

Figure 1:
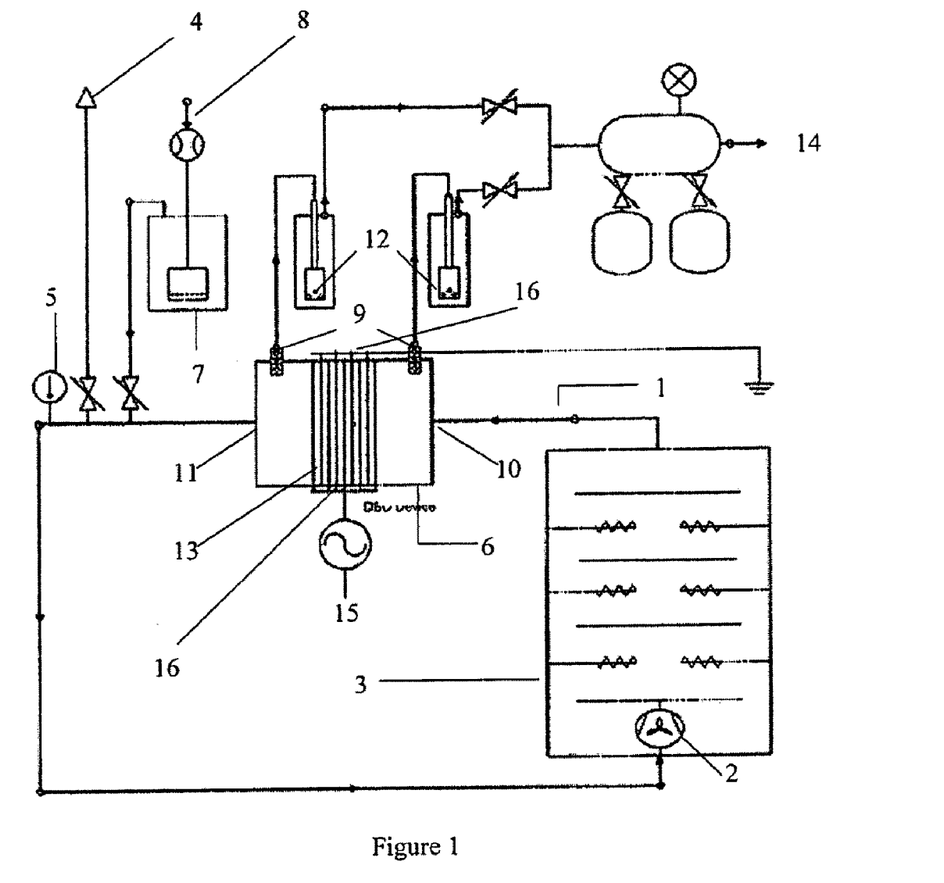
FIG. 1 is a schematic of the Pathogen Detection and Remediation Facility (PDRF).

The PDRF system, shown in FIG. 1, is a bioaerosol treatment facility designed to provide a recirculating gaseous media environment. Because the PDRF system is capable of recirculating airflow, bioaerosols entrained, dispersed or suspended in the gaseous media can be treated with repeated passes through the same plasma discharge. Additionally, a sealed, recirculating system allows for complete control over relative humidity inside the system, which is important because even small fluctuations in relative humidity have been shown to significantly decrease the survivability of airborne bacteria. The PDRF system was designed as a plug flow reactor, such that airflow inside the system is turbulent, minimizing radial variation of the bacterial concentration in the airflow.

The PDRF system has a total volume of 250 liters and is designed to operate at high airflow rates of at least 25 L/s, which is typical of indoor ventilation systems. The system has an inlet with an attached Collison nebulizer for bioaerosol generation and two air-sampling ports connected to a vacuum air sampling system. The system also has a large mixing chamber that contains a series of aluminum baffle plates and a variable speed centrifugal blower motor 2 that drives the air through the DBD treatment chamber 6. The residence time, that is, the time for one bioaerosol particle to make one complete revolution through the system, is approximately 10 seconds.

Figure 2:
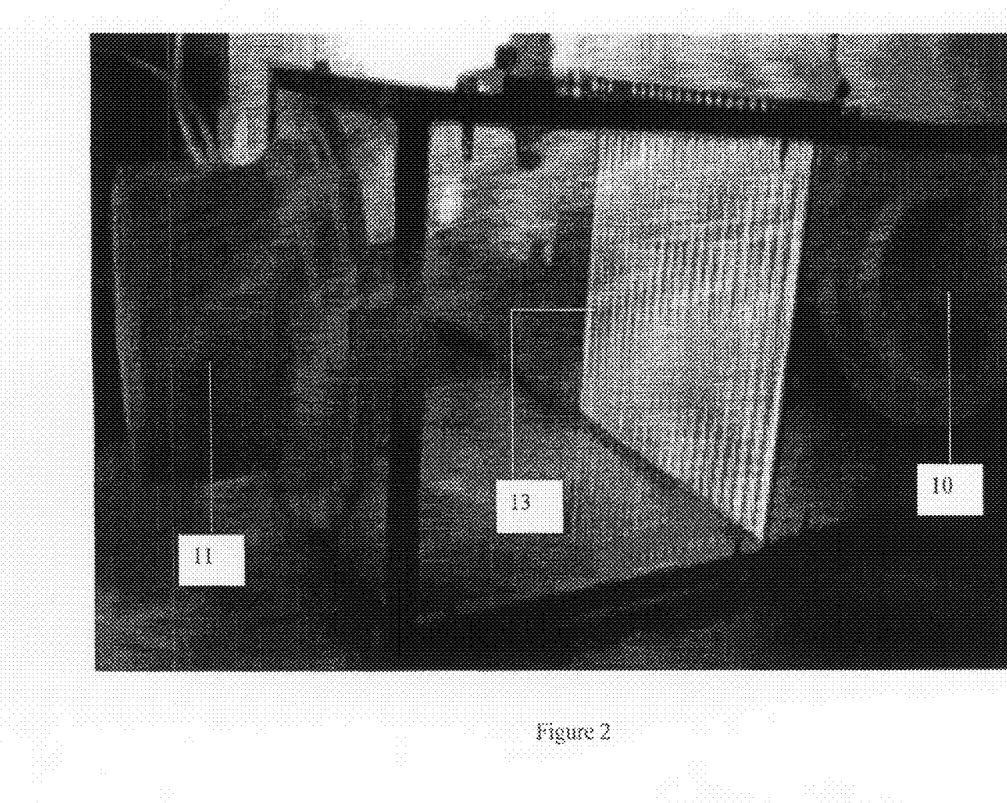
FIG. 2 is a depiction of a DBD gaseous media sterilization device.

The DBD device 6, shown in FIG. 2, may include of a thin plane of wires with equally spaced air gaps of 1.5 mm, and each second wire is a high voltage electrode 16. The high voltage electrodes 16 are about 1 mm diameter copper wires shielded with a quartz capillary dielectric that has an approximate wall thickness of 0.5 mm. The total area of the DBD including electrodes is 214.5 cm$^2$ and without electrodes is 91.5 cm$^2$. The DBD device 6 further has two air sample ports 9 located at a distance of 10 cm from each side of the discharge area so that bioaerosol can be sampled immediately before and after it enters the plasma discharge. When the PDRF system is operated at a flow rate of 25 L/s, the air velocity inside the DBD chamber is 2.74 m/s and the residence time of one bioaerosol particle, containing one *E. Coli* bacterium, passing through the DBD is approximately 0.73 milliseconds.

Figure 3:
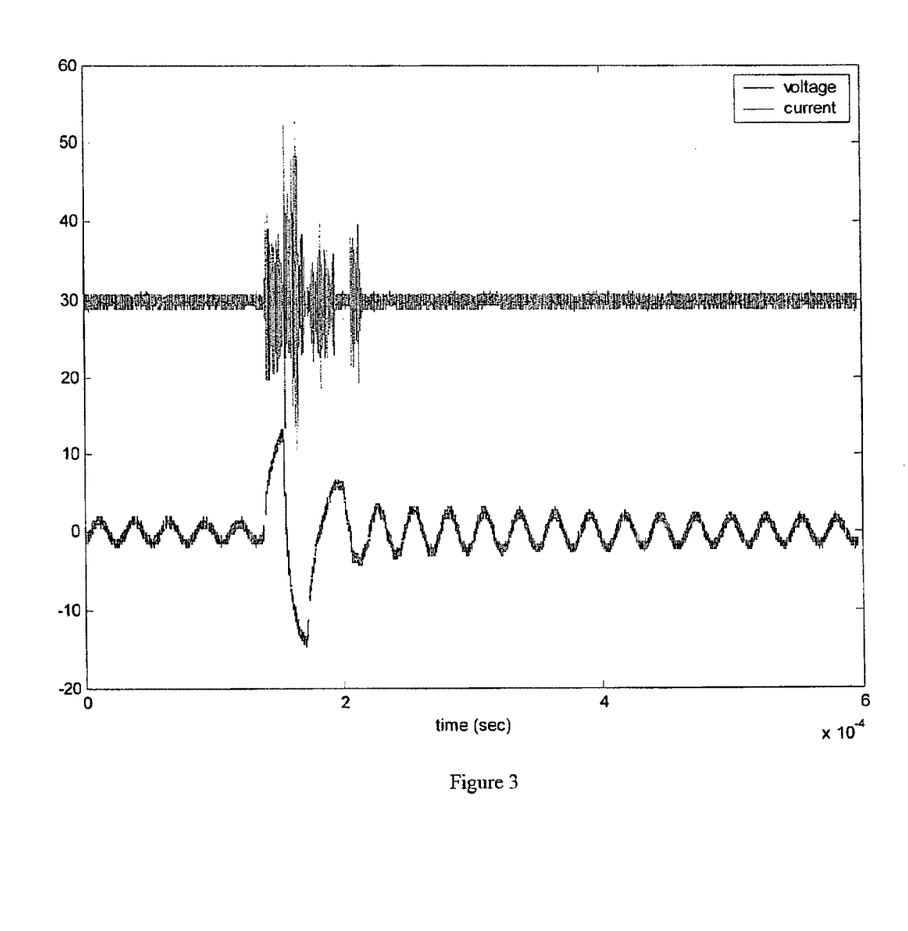
FIG. 3 is a graph of a current and voltage waveform of the DBD device. Lower curve is voltage signal in kilovolts (kV), upper curve is current signal in amperes (A).

The DBD device 6 is operated using a quasi-pulsed power supply 15 that delivers a quasi-sinusoidal voltage waveform with a very fast rise time that nearly simulates a true square wave pulse, as shown in FIG. 3. The period between pulses is approximately 600 μs, peak-to-peak voltage is 28 kV, and current pulses that pass through air plasma reach 50 amps. The average power of the discharge is approximately 330 watts. The average discharge area is approximately 91 cm$^2$, and the average power density is 3.6 watts/cm$^2$. The majority of power is discharged in the very short duration of the pulse itself, which has a period of 77 μs and average pulse power of 2618 W. Since the residence time of a bioaerosol particle passing through the discharge area is 0.73 ms and the period between pulses is 0.6 ms, assuming the discharge is fairly uniform and there are no gaps between streamers, each bioaerosol particle that passes through the DBD experiences about 1 pulse of DBD power.

Example 2

The effectiveness of the present method was tested on *Escherichia Coli* (K-12 strain). The present invention was found to effectively render 99% of the viable *E. Coli* inactive.

Each culture of *E. Coli* (K-12 strain) used in this study was prepared in a 250 ml flask containing LB growth medium and was incubated overnight for about 12 hours at 37° C. with constant mixing on a water bath shaker. The culture was then centrifuged at 3500 rpm for a period of 10 minutes and rinsed with a sterile phosphate buffered saline (PBS) solution (1× concentration). This procedure was repeated three times to ensure complete removal of growth medium and to concentrate the culture to a volume of 45 ml for nebulization.

After the PDRF system was pre-sterilized using the internal heating system 5 and pre-humidified to a relative humidity of about 70%, the bacteria culture was placed into a BGI 24-jet Collison nebulizer, and the nebulizer was operated at 40 psi for a period of 45 seconds at a nebulization rate of about 1.1 ml/min. The DBD device 6 was then switched on for a period of 10 seconds, and the first two air samples were immediately and sequentially taken before and after plasma treatment. The discharge time of 10 seconds was selected to correspond with the residence time of the bioaerosol to make one complete revolution in the PDRF system. The samples measure the decontamination effectiveness of DBD on a per pass basis, ensuring that each bioaerosol particle has been treated once by the discharge. Another set of air samples was taken approximately 2 minutes later to accommodate the amount of time required to remove and replace the air samplers with the next set of pre-sterilized samplers. This process was repeated again until the typical number of air samples, approximately six, was achieved. Each of the pre-sterilized air samplers was initially filled with 30 ml of sterile PBS solution, and after sampling, each solution was transferred to a sterile 50 ml centrifuge tube for assaying.

Following each experiment, liquid samples from each impinger 12 were transferred to 50 ml centrifuge tubes and serially diluted in PBS, plated onto LB agar plates, and incubated at 37° C. overnight. Visible colonies were counted and recorded within the following 24-hour period.

Additionally, a fluorescent method of bacteria detection, flow cytometry, was also employed to detect the presence of *E. Coli* in each air sample taken during experiments. It is important to verify the presence of inactivated bacteria because it eliminates the possibility that DBD could act as an electrostatic precipitator, which could charge the bioaerosol droplets and remove them from the airflow inside the PDRF system. Whereas colony counting techniques are limited to detecting only viable bacteria, flow cytometry is capable of detecting the presence of bacteria whether it is viable or inactivated. This technique utilizes two fluorescent dyes; SYBR Green I to detect the presence of all bacteria (dead and alive), and propidium iodide (PI) to detect the bacteria with disintegrated cyto-plasmic membranes.

Figure 5:
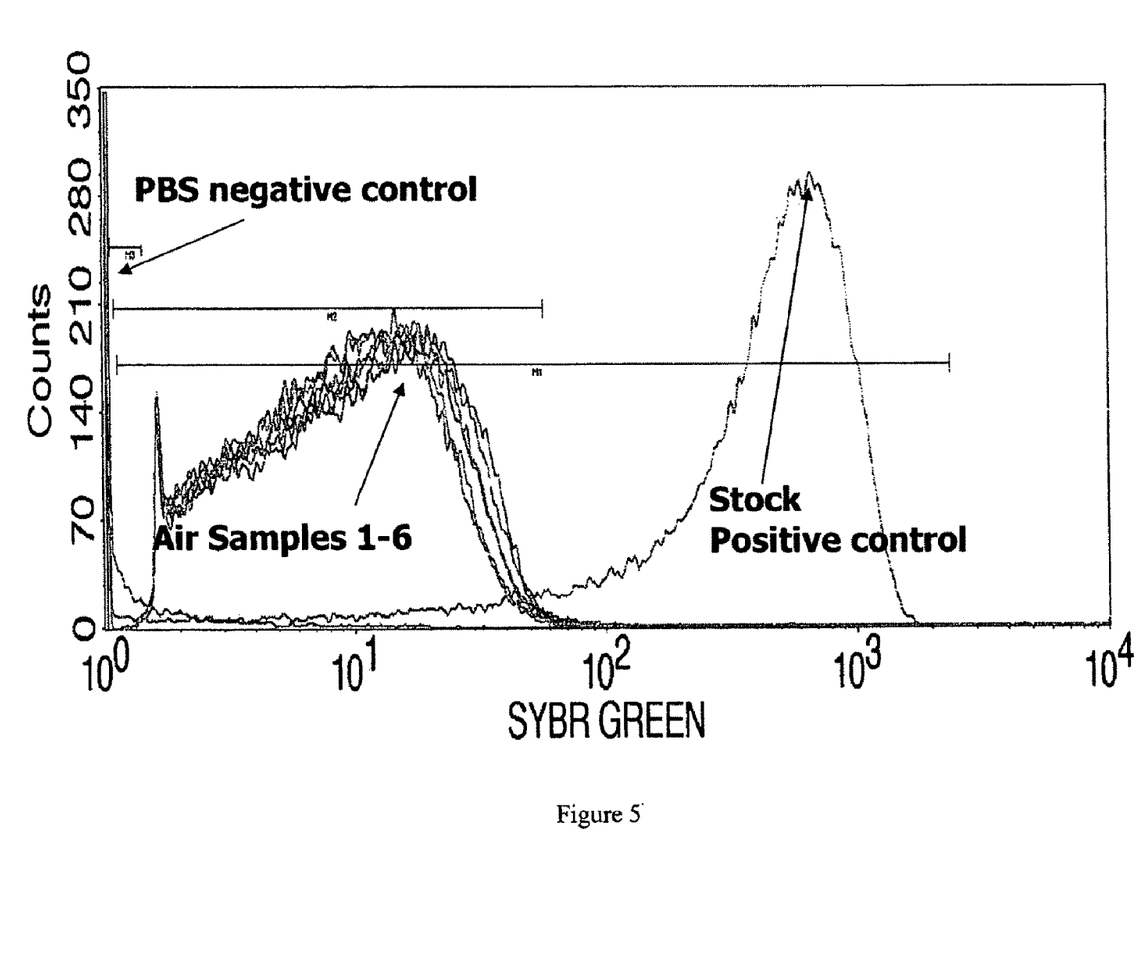
FIG. 5 is a flow-cytometric histogram for the total number of E. Coli (alive+dead) stained by SYBR Green I.

FIG. 5 shows flow cytometry results for the DBDG-treated air samples using only SYBR Green I florescent dye. The florescent intensity peak for air samples one through six is identical, which means that there are the same number of total bacteria present for each air sample taken during experiments. The stock positive control sample is a pure unaltered sample of *E. Coli* whose intensity peak was two orders of value greater than the intensity of the air samples. Additionally, the intensity of propidium iodide red fluorescence (not shown) was found to be negligible in comparison with expected PI positive control and therefore the outer membranes of *E. Coli* were not disintegrated after interaction with DBDG.

The cytometry results show that DBD plasma is acting not as an electrostatic precipitator, but as a device capable of decontaminating high concentrations of bacterial bioaerosol in flight at high flow rates in a laboratory scale ventilation system.

An interesting yet unexpected decrease in bacterial concentration is shown between samples 2 and 3 of the DBD-treated trial in which the number of viable bacteria dropped to zero. It is not immediately clear how such a drastic change could have occurred especially since the plasma discharge was turned off during this period. Additionally, it is not fair to claim that this second drop in concentration is an additional 4-log reduction because the sampling system efficiency is low (6%±3%) and zero bacteria present in the air samplers could mean that there are indeed viable bacteria present in the system, but its out of the range of our detection limits.

Having described the preferred embodiments of the invention which are intended to be illustrative and not limiting, it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, the intended scope of protection is set forth in the appended claims.

The invention claimed is:

1. A method for sanitizing a gaseous medium, the gaseous medium comprising a biologic agent entrained, dispersed or suspended in the gaseous medium, the method comprising the steps of:
    (a) generating a non-thermal plasma discharge curtain having an input power, W, and characterized as having a free area, S, said non-thermal plasma discharge curtain positioned so that the gaseous medium having a volumetric flow rate, Q, can pass through the free area of the non-thermal plasma discharge curtain, such that the ratio of input power to volumetric flow rate, W/Q, is in the range of between 3 and 100 joules per liter;
    (b) passing the gaseous medium through the non-thermal plasma discharge curtain, thereby contacting the biologic agent entrained, dispersed or suspended in the gaseous medium with the non-thermal plasma discharge so as to render a portion of said biologic agent inactive.

2. The method of claim 1, wherein the non-thermal plasma is generated in a dielectric barrier discharge.

3. The method of claim 2, wherein the dielectric barrier discharge is generated using a series of voltage pulses between electrodes, having a thickness, d, relative to the flow of the gaseous medium, such that the residence time of the biologic agent within the non-thermal plasma discharge curtain is about the same time or longer than the time between the high voltage pulses.

4. The method of claim 1, wherein the non-thermal plasma discharge is generated by a high frequency oscillation of voltage of about 1 kHz to about 20,000 kHz.

5. The method of claim 1, wherein the non-thermal plasma discharge is generated by a high frequency oscillation of voltage of about 5 kHz to about 30 kHz.

6. The method of claim 4, wherein the high frequency oscillation is generated by applying a voltage of about 1 kV to about 50 kV.

7. The method of claim 4, wherein the high frequency oscillation is generated by applying a voltage of about 5 kV to about 30 kV.

8. The method of claim 1 wherein the biologic agent is selected from the group consisting of at least one bacterial agent, at least one viral agent, at least one spore agent and a mixture thereof.

9. The method of claim 1 wherein the ratio of input power to flow rate is in the range of between 5 and 30 joules per liter.

10. The method of claim 1, wherein the non-thermal plasma discharge is generated in a magnetically-rotating gliding arc.

* * * * *